United States Patent
Sarpeshkar et al.

(10) Patent No.: US 10,434,313 B2
(45) Date of Patent: Oct. 8, 2019

(54) MULTI-ELECTRODE, ENERGY-RECYCLING, RESONANT STIMULATION CIRCUITS AND ARCHITECTURES FOR NERVE BLOCKING

(71) Applicant: Rahnix, Inc., Hanover, NH (US)

(72) Inventors: Rahul Sarpeshkar, Hanover, NH (US); Woradorn Wattanapanitch, Bangkok (TH)

(73) Assignee: Rahnix, Inc., Hanover, NH (US)

(*) Notice: Subject to any disclaimer, the term of this patent is extended or adjusted under 35 U.S.C. 154(b) by 62 days.

(21) Appl. No.: 14/953,343

(22) Filed: Nov. 28, 2015

(65) Prior Publication Data
US 2017/0143969 A1    May 25, 2017

Related U.S. Application Data

(60) Provisional application No. 62/085,526, filed on Nov. 29, 2014.

(51) Int. Cl.
*A61N 1/00* (2006.01)
*A61N 1/36* (2006.01)
*A61N 1/05* (2006.01)

(52) U.S. Cl.
CPC ....... *A61N 1/36125* (2013.01); *A61N 1/0551* (2013.01); *A61N 1/36071* (2013.01); *A61N 1/36128* (2013.01)

(58) Field of Classification Search
CPC .............. A61N 1/0551; A61N 1/36125; A61N 1/36071; A61N 1/36128
See application file for complete search history.

(56) References Cited

U.S. PATENT DOCUMENTS

2015/0174397 A1* 6/2015 Bhadra ................ A61N 1/0556
607/117

* cited by examiner

*Primary Examiner* — Mallika D Fairchild
(74) *Attorney, Agent, or Firm* — Davis & Bujold PLLC; Michael J. Bujold

(57) ABSTRACT

We disclose multi-electrode, energy-recycling, resonant stimulation circuits and strategies for energy-efficient blocking of action potentials in nerve. Our schemes increase the probability that most of the electrical stimulation is directed through the nerve rather than dissipated in ohmic extracellular solution alongside it via mechanical and electrical means; they use energy-recycling and resonant-amplification strategies that recycle and amplify capacitive nerve energy such that the nerve itself becomes an integral part of the circuit creating its oscillatory blocking waveform; they use traveling-wave strategies with distributed multi-electrode stimulation that alters the timing and intensity of stimulation at various points along the nerve to synchronize blocking stimulation with wave propagation in the nerve in an energy-efficient fashion. The schemes operate synergistically in a medical device to create advanced energy-efficient nerve-blocking stimulators whose operation may be altered and adapted in a feedback fashion to sensed action potentials in the nerve.

17 Claims, 15 Drawing Sheets

MULTI-ELECTRODE, ENERGY-RECYCLING, RESONANT STIMULATION CIRCUITS AND ARCHITECTURES FOR NERVE BLOCKING

CROSS REFERENCE TO RELATED APPLICATIONS

This application claims benefit under 35 USC § 119(e) of U.S. Provisional Patent Application Ser. No. 62/085,826 filed on Nov. 29, 2014, the contents of which are incorporated herein in their entirety by reference.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

BACKGROUND

Action potential propagation can be blocked in nerves by alternating current excitation, as is described for example in J. Tanner, "Reversible Blocking of Nerve Conduction by Alternating Current Excitation", NATURE, Vol. 195, pp. 718-719, Aug. 18, 1962. Typically, a relatively large pair of neighboring cuff electrodes circumferentially surround the nerve with a small lateral distance between them. A high-frequency a.c. waveform, usually in the 1 kHz to 100 kHz frequency range creates an oscillatory current or voltage waveform between these electrodes. Due to the small impedance of the extracellular solution separating the two electrodes—for example, this impedance has a value of approximately 50Ω from a typical 5 V/100 mA measurement—these conventional stimulation systems dissipate a lot of energy as ohmic loss instead of directing the energy efficiently to induce nerve blocking. In fact, the energy consumption of current stimulation systems for nerve blocking is very high compared with those of even the most power-hungry FDA-approved stimulators for nerve excitation. Thus, for long-term clinical use in human beings, circuits and architectures for nerve-blocking a.c. stimulation with a much higher energy efficiency than that of the current systems are needed.

Prior patent-granted work as described in S. Arfin and R. Sarpeshkar, "An Electrode Stimulator with Energy Recycling and Current Regulation", U.S. Pat. No. 8,700,144 B2, Issued Apr. 15, 2014, has used an inductor to recycle capacitive energy in an electrode impedance, shuttling this energy back and forth between a storage capacitance and electrode capacitance to lower power dissipation in nerve stimulation. This strategy enables the creation of a switching power supply that adaptively and adiabatically adjusts its compliance voltage to be just a little bit higher than that of the electrode voltage, thus minimizing ohmic losses. The differential value between the power supply and electrode voltage is regulated via a feedback loop to maintain constant-current stimulation into the electrode. The savings in power are near the fundamental limits of physics set by ohmic solution resistance. In most nerve stimulators that excite the nerve, electrode impedances are dominant such that this power scheme is as nearly optimal as it can be: one cannot dissipate less power than that caused by current flowing through an ohmic solution resistance. However, in blocking nerve stimulators, electrode impedances are typically not dominant such that it is the nerve impedance energy itself that needs to be recycled, not the electrode impedance energy. Furthermore, the waveform required for stimulation needs to be an oscillatory a.c. waveform such that the adiabatic switching power-supply techniques are not a power-efficient method for creating such a waveform.

The system described in Franke, Kilgore, and Bhadra, "Systems and Methods that Provide an Electrical Waveform for Neural Stimulation or Nerve Block" focuses on methods to achieve an oscillatory waveform with charge balancing but has little impact on energy: It creates an oscillatory waveform in one circuit component, ensuring that it is charge balanced in another circuit component, and then couples the final output of the second circuit component as an electrical waveform suitable for nerve stimulation or blocking. One embodiment described in Franke et al. uses an inductor. It is easy to create an oscillator with an inductor as is well known in elementary electrical engineering, physics, and in the public domain, for example, see R. Sarpeshkar, "Ultra Low Power Biolectronics: Fundamentals, Biomedical Applications, and Bio-inspired Systems", Cambridge University Press, 2010. However, if the nerve and electrodes are separated from the waveform generators that create the oscillation, and not part of it, the nerve capacitive energy does not resonate with the inductor, just the capacitive energy of a circuit component in the oscillator. Thus, there is little energy benefit, and not surprisingly, none claimed.

BRIEF SUMMARY OF THE INVENTION

In this application, we disclose circuits and architectures for reducing energy and power consumption of nerve-blocking stimulation systems. These embodiments include but are not limited to i) the use of passive inductive, active inductive, active transconductor-capacitor, or piezoelectric strategies that serve to resonantly amplify and/or recycle capacitive nerve energy such that the nerve itself becomes an integral part of the circuit that creates its oscillatory blocking waveform; ii) mechanical multi-electrode configurations and stimulation paradigms that help increase the probability that most of the stimulation current is directed through the nerve rather than dissipated in ohmic extracellular solution alongside it; iii) the use of multi-electrode traveling-wave architectures that alter the timing and intensity of stimulation at various points along the nerve to synchronize blocking stimulation with traveling-wave propagation in the nerve in an energy-efficient and selective fashion; iv) the use of feedback or calibration loops to configure these stimulation systems such that they operate at resonance and with mechanical/electrical electrode configurations that maximize blocking effectiveness and energy efficiency.

We disclose that one can actually use either passive or active inductors to recycle or resonantly amplify the reactive energy in the nerve itself, shuttling energy back and forth between inductive and capacitive forms, to create a resonant oscillatory system. The nerve itself becomes an integral and inseparable part of a low-energy circuit that creates its oscillatory blocking waveform. That is, our invention uses the nerve itself to make an oscillatory system, rather than making a separate high-energy-consuming oscillatory system to drive the nerve as in all prior work. We can thus aim to achieve energy efficiency set by the fundamental limits of physics of reactive nerve impedance, the best that is possible in any design.

Some embodiments of our invention use gyrated-capacitance implementations of inductors with active transconductors rather than passive inductors to create a more compact implementation. Those of ordinary skill in the art will appreciate that other active transconductor-capacitor circuits as are well known in low-power circuit design can provide alternative energy-efficient active implementations as well. Adaptive versions of our embodiments sense action potentials in the nerve to alter the parameters or topology of our nerve stimulator to offer maximal energy efficiency and to ensure operation at resonance.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

DETAILED DESCRIPTION

The Bridge-Cuff Blocking Stimulator

The 'bridge cuff blocking stimulator', which represents one embodiment of our invention, has two partially circumferential electrodes above the nerve, separated from each other by a small lateral distance as in current blocking stimulators. In addition, it has two partially circumferential electrodes below the nerve in symmetric locations, also separated from each other by the same lateral distance. Unlike a current blocking stimulator, we ensure that the lateral voltage drop across neighboring electrodes either below or above the nerve is always small. Thus, the lateral impedance of approximately 50Ω (estimated from 5V/100 mA measurements in traditional blocking stimulators) always develops little voltage across it and does not dissipate power by design. A feedback loop in a current-stimulation strategy can enforce this adiabatic voltage constraint across two electrodes through various means. In a voltage-stimulation strategy, two electrode voltage drives architected to always have a small differential voltage between them can enforce this constraint more easily.

Figure 1:
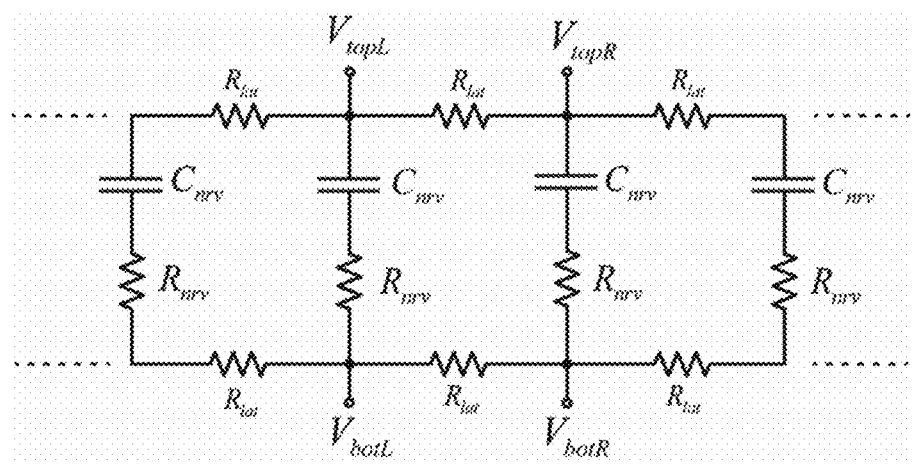
FIG. 1 shows the effective nerve impedances seen by a four-electrode bridge-cuff electrode with two cuff electrodes above the nerve, and two cuff electrodes below the nerve at a given blocking frequency of stimulation.

To help steer current through the nerve, we intentionally architect larger voltages across vertically separated electrodes by driving these electrodes in an anti-phasic fashion (via current or voltage). If the electrode impedances are designed to be small, as in current high-frequency blocking stimulators, then the impedance across two vertically separated electrodes in the bridge will be dominated by the actual electrical impedance of nerve and the solutions surrounding it. Thus, it can be modelled by an effective $R_{nrv}$ and $C_{nrv}$ in series that represent the complex impedance of the fascicles, epineuria, intra and extracellular solutions, nerve-membrane capacitance and other components, for example, as described in A. R. Kent and W. M. Grill, "Model-based analysis and design of nerve cuff electrodes for restoring bladder function by selective stimulation of the pudendal nerve", Journal of Neural Engineering, 10 (3), June 2013. Regardless of the complexity of the actual nerve, or even if electrode impedances are not negligible, at a given amplitude and frequency of oscillation, the overall electrical impedance can still be represented by a Thevenin equivalent of the net reactance and net resistance at this frequency, due to contributions from all sources. The Thevenin equivalent is valid for small deviations around the oscillation amplitude, and described by an effective describing function. Similarly, the lateral ohmic solution resistance between horizontal electrodes either at the top or bottom may be represented by $R_{lat}$. These impedances are shown in FIG. 1. They bridge the top-left ($V_{topL}$), top-right ($V_{topR}$), bottom-left ($V_{botL}$), and bottom-right ($V_{botR}$) corners at which the four cuff electrodes are located.

Figure 2:
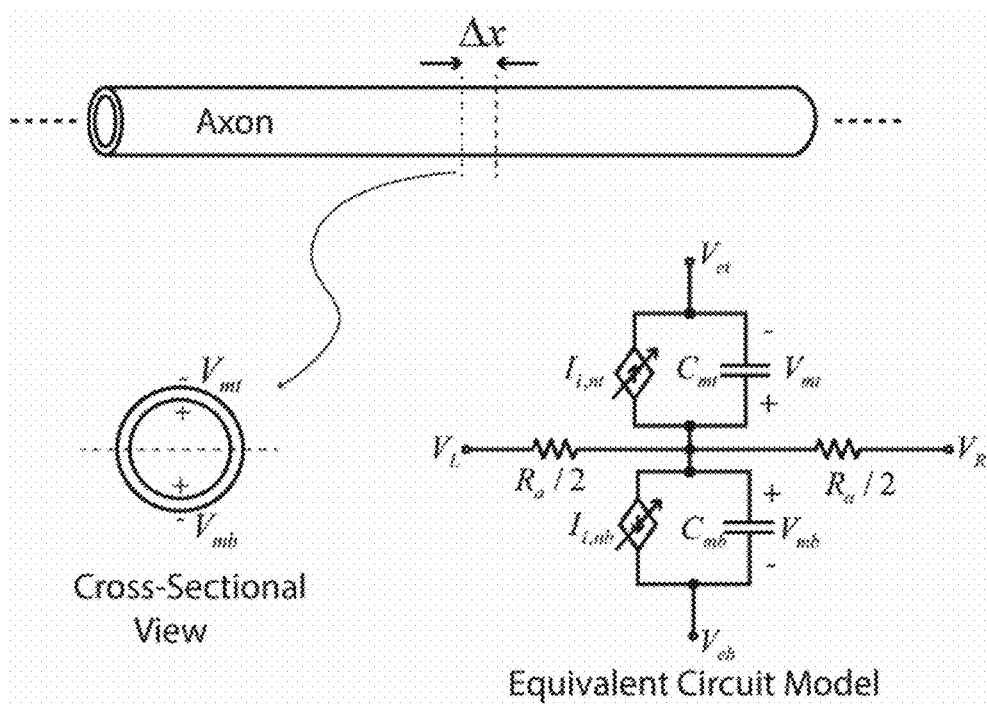
FIG. 2 shows how an axon nerve fiber can be modeled as a cascade of lumped passive and active distributed circuit elements.

Driving vertically-separated electrodes anti-phasically helps steer the stimulation current through the nerve and, as a result, through the axons inside the nerve: FIG. 2 shows a standard Hodgkin-Huxley model of the axon; the cylindrical-shaped axon is divided into small compartments, each one with a length of Δx. If Δx is sufficiently small, we can represent each compartment using a lumped circuit model. We can then model each compartment with two half membranes: the top membrane and the bottom membrane, each one having a separate membrane potential ($V_{mt}$ and $V_{mb}$) to control the dynamics of its ion channels. The circuit model of each compartment is shown in on the bottom right of FIG. 2; $C_{mt}$ and $C_{mb}$ represent the membrane capacitances of the top and bottom half membranes, respectively; $I_{i,nt}$ and $I_{i,nb}$ are the voltage-controlled current sources that represent the effective total ionic currents that flow out of the compartment through the top and bottom half membranes, respectively. $I_{i,nt}$ is controlled by the top membrane's potential $V_{mt}$ while $I_{i,nb}$ is controlled by the bottom membrane's potential $V_{mb}$. Each axon compartment is coupled to the adjacent compartments with the resistance $R_a/2$ where $R_a$ is the total longitudinal resistance of the compartment due to intracellular fluid inside the axon.

Figure 3A:
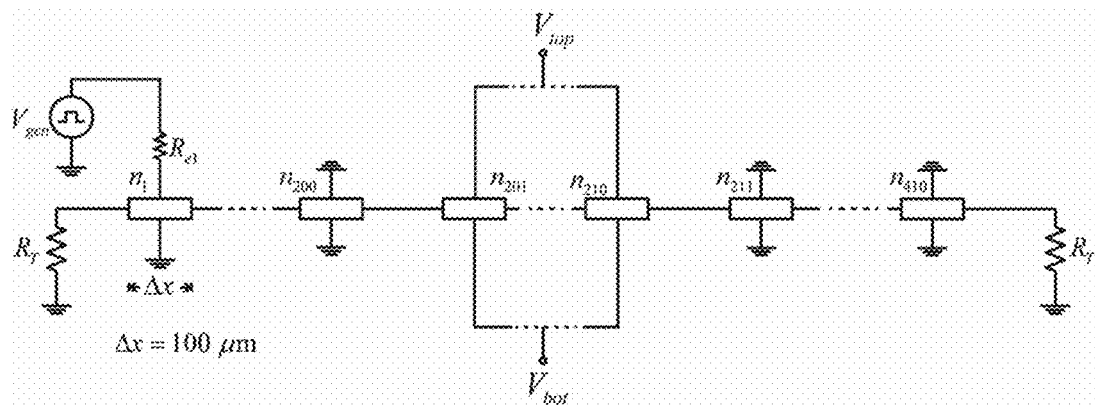
FIG. 3A shows a distributed axon nerve fiber with electrical stimulation that launches an action potential at its left end. Blocking stimulation in the center prevents action-potential propagation to the right of the blocking site.
Figure 3B:
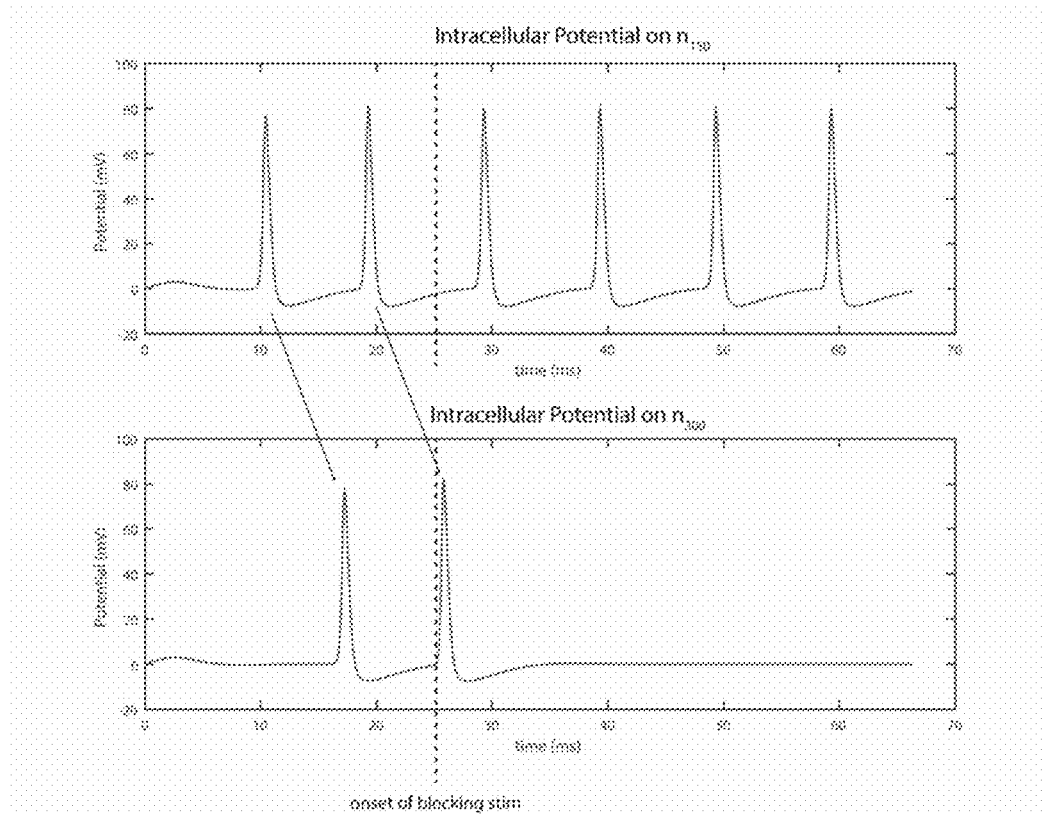
FIG. 3B shows that action potentials that arise before blocking is initiated propagate to a distal location to the right of the blocking site. However, action potentials that arise after blocking is initiated do not.

To emulate the blocking mechanism seen in nerves, we chain 410 axon compartments together to form a long axon as shown in FIG. 3A. In this model, we terminate the two ends of the axon with $R_T$, which is equal to the input resistance into an infinitely-long axon with the same diameter. With Δx=100 μm, the total length of our axon is 4.1 cm. We then stimulate one end of the axon with the pulse source $V_{gen}$ to generate spikes that propagate through the axon. A high-frequency sinusoidal blocking waveform is differentially applied across $V_{top}$ and $V_{bot}$ nodes on the compartments $n_{201}$ to $n_{210}$-these compartments are 2 cm away from the origin of the spikes as in many typical research or clinical applications. Our simulations show that, for an axon with a diameter of 50 μm, we only require $|V_{top}-V_{bot}| \approx 200$ mV$_{pp}$ to make the latter compartments refractory and to thus block the action potential propagation in the axon; the stimulation waveform is a 20-kHz sinusoidal voltage. FIG. 3B shows the intracellular potentials in the $n_{150}$ and $n_{300}$ compartments. The blocking stimulation waveform is applied at t=25 ms. Before the blocking stimulation is applied, spikes from $n_{150}$ reach $n_{300}$ in an unblocked fashion. However, once the blocking stimulation is applied, spikes from the $n_{150}$ compartment can no longer reach the $n_{300}$ compartment, indicating that the axon is blocked at the stimulation site.

Figure 4:
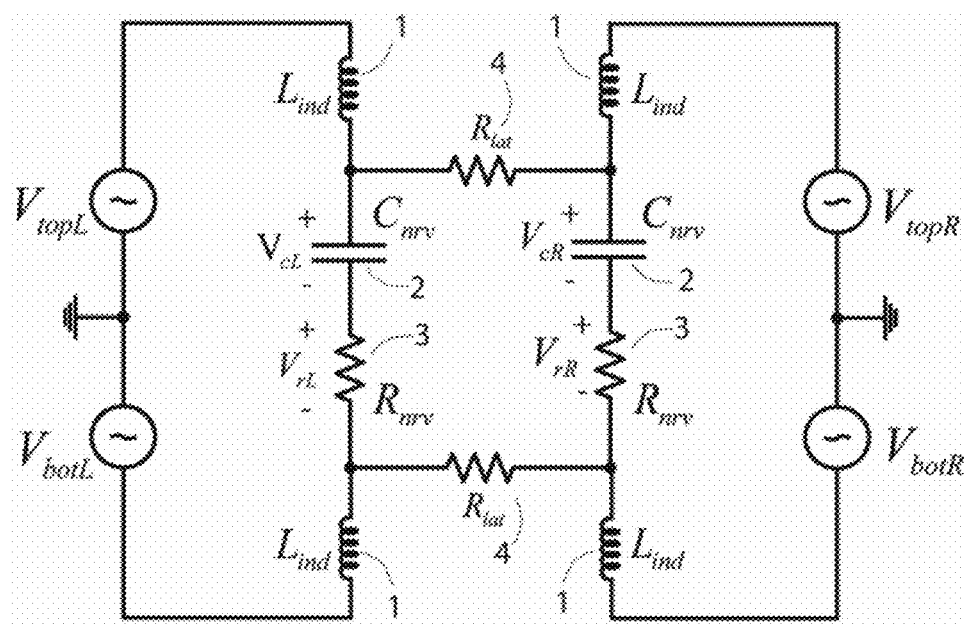
FIG. 4 shows how the nerve itself can form part of an energy-efficient resonant oscillator in a bridge-cuff blocking stimulator. The inductors recycle and build up the capacitive nerve energy over many cycles causing the capacitive nerve voltage to be a resonantly amplified version of the input drive voltage.
Figure 5:
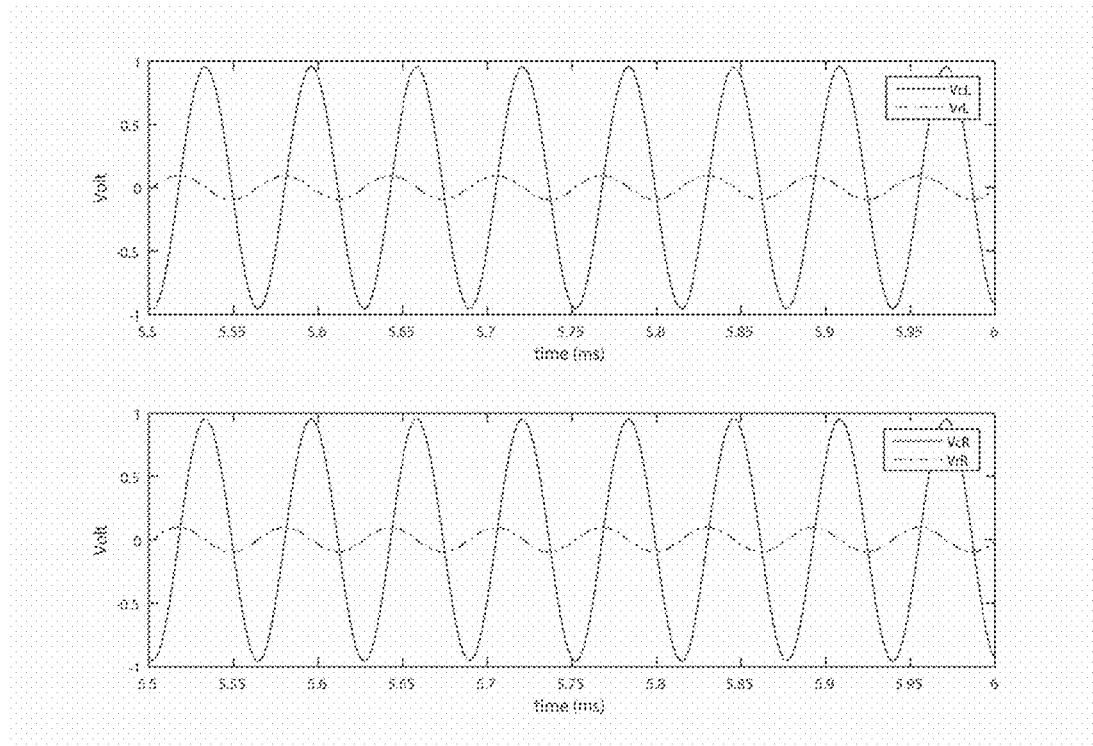
FIG. 5 shows resonant amplification of the input drive voltage in a bridge-cuff blocking stimulator.

One key to being energy efficient in blocking stimulation is to develop this axonal excitation with as little stimulation voltage as possible. FIG. 4 shows how we can achieve resonant amplification and energy recycling within a bridge cuff: Inductors $L_{ind}$ 1 resonate with $C_{nrv}$ 2 in each vertical series resonance circuit, driven by anti-phasic voltage sources $V_{topL}$ and $V_{botL}$ and $V_{topR}$ and $V_{botR}$ respectively. The lateral voltages $|V_{topL}-V_{topR}|$ and $|V_{botL}-V_{botR}|$ are always maintained to have a relatively small magnitude. The inductive energy recycling of capacitive energy and vice versa over many cycles of stimulation can amplify the voltage drop across $C_{nrv}$ 2 to be significantly higher than that across $R_{nrv}$ 3, thus enabling blocking via refractory nerve stimulation more easily. Indeed, FIG. 5 shows even 100 mV voltages on all four bridge cuff electrodes can amplify the effective voltage across $C_{nrv}$ by about a factor of 10 compared with that across $R_{nrv}$ to create a 1 V amplitude. To do so, $L_{ind}$ 1 and the frequency of stimulation are appropriately chosen. Furthermore, we always maintain a low lateral voltage drop across the ohmic solution resistance $R_{lat}$ (top and bottom traces are nearly identical w.r.t. corresponding voltages).

With this embodiment of the invention, by forcing the voltage drop across $R_{lat}$ to be small through the amplitude and timing control of the stimulation voltages, a value of $R_{nrv}$ of 1 kΩ already saves 20× power over a conventional two-electrode blocking cuff. In addition, it can save about 10× power via resonant effects: a 100 mV stimulation yields 1 V reactive excitation across $C_{nrv}$ that would otherwise need 10× larger voltages in the conventional scheme. Thus, an overall savings of 200× in power may be achievable.

A Bridge Cuff with Insulating Wings

Figure 6:
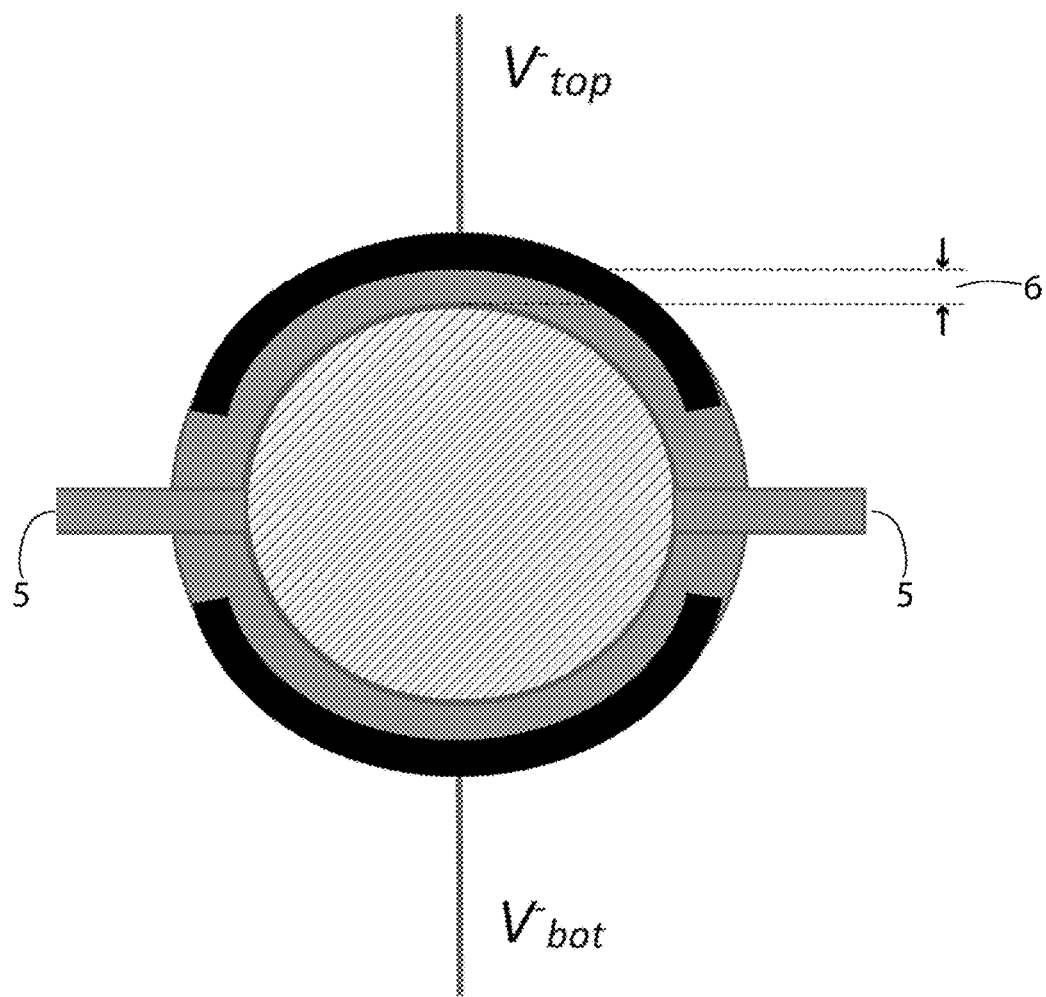
FIG. 6 shows a bridge-cuff electrode stimulator in cross section along the nerve that has 'wings' (marked as 5 in the figure). The insulating wings minimize the probability that current will take an extracellular path between the top and bottom electrodes of the cuff rather than a current path through the nerve.

FIGS. 4 and 5 indicate that we want the effective $R_{nrv}$ across vertical cuff electrodes to be small to get maximum resonant amplification and low loss. There is not much that we can do w.r.t. resistance within the nerve except for attempting to get multi-electrode arrays closer to regions of interest; furthermore, the small distance between the top and bottom cuff vertical electrodes minimizes this resistance anyway. However, we may want to minimize ohmic shunting loss through extracellular solution outside the nerve between top and bottom electrodes. FIG. 6 shows a mechanical topology in one embodiment in cross section along the nerve that helps in this regard: Mechanical wings 5 that extend the grey insulating substrate on which the black metallic electrodes normally reside and a small electrode-to-nerve distance 6 lengthen shunting paths outside the nerve between vertical cuff electrodes compared to paths within the nerve, thus reducing their contribution to $R_{nrv}$.

Traveling-Wave Multi-Electrode Stimulation

Nerve conduction block from high-frequency stimulation occurs from the modulation of the axon's membrane potential, which alters the dynamics of the voltage-gated ion channels on the membrane and prevents the propagation of the action potentials. In myelinated axons, ion channels are clustered at the nodes of Ranvier (NRV)-gaps in the myelin sheath that play important roles in speeding up the action potential propagation—whose internode distance can be quite large (sometimes up to 1.5 mm). One important question arises regarding our proposed vertical driving scheme using the bridge cuff electrodes: How do we surgically place the top and bottom cuff electrodes right on top of a NRV such that the ion channels underneath are directly modulated? Due to the random nature of NRV's internode distance, it is likely that the placed cuff electrodes may miss the NRV, reducing the effectiveness of the stimulation, especially when the electrodes are placed very close to the nerve to minimize $R_{nrv}$. Conventional blocking schemes avoid the issue by directing a very large stimulation current along the lateral distance of the nerve, thus increasing the probability that some small fraction of the stimulation current may get to the ion channels located between the two lateral electrodes. As we have discussed, this conventional scheme incurs high power dissipation due to high ohmic loss.

Figure 7:
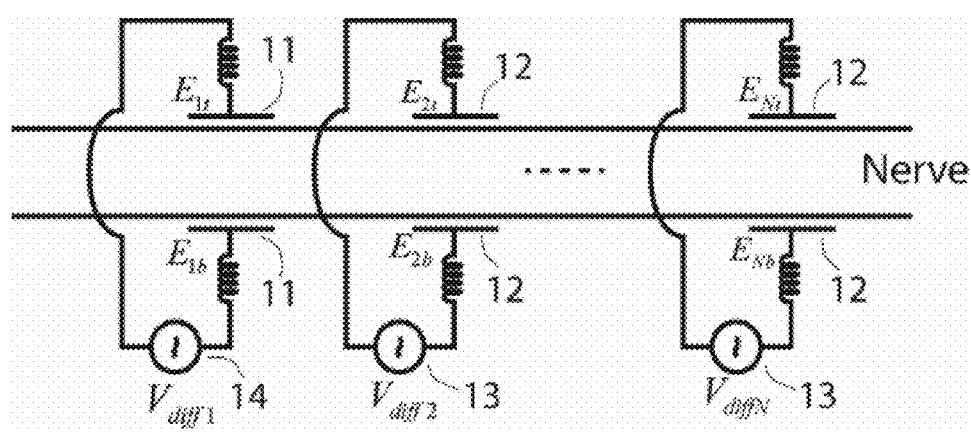
FIG. 7 shows a multi-electrode traveling-wave blocking stimulator with inductive energy-recycling and resonant amplification at each electrode site.

The embodiment disclosed in FIG. 7, termed "Traveling-wave multi-electrode stimulation", aims to maximize the effectiveness of stimulation while avoiding high ohmic loss. The scheme enables one to maximize the amplitude of the membrane potentials along the lateral distance of the axon with low overall stimulation power. In FIG. 7, if we stimulate the $E_{1t}$-$E_{1b}$ electrode pair 11, the amplitude of the membrane potential of the axons right under the $E_{1t}$-$E_{1b}$ pair 11 is maximized but decays exponentially along the lateral distance of the axon. We may consider the membrane potential as a wave that propagates along the axonal cable. Being lowpass in nature, the axonal cable attenuates the membrane potential wave as it moves away from the origin, thus reducing the effect of stimulation on the ion channels away from the stimulation site. However, at optimal distances along the nerve away from the $E_{1t}$-$E_{1b}$ electrode pair, if we place other pairs of electrodes ($E_{2t}$-$E_{2b}$, ..., $E_{nt}$-$E_{Nb}$ 12) and stimulate them anti-phasically with the right timing $V_{diff2}$, ..., $V_{diffN}$ 13 introducing proper phase delays with respect to $V_{diff1}$ 14—we can create constructive interference with the membrane potential wave that travels from the $E_{1t}$-$E_{1b}$ pair 11. Thus, with lower stimulation levels (and lower power consumption) compared to that applied to the $E_{1t}$-$E_{1b}$ pair 11, the other electrode pairs 12 may still elicit the same membrane potential amplitude in the axons underneath them, increasing the probability of modulating ion channels along the lateral distance of the axons.

Figure 8A:
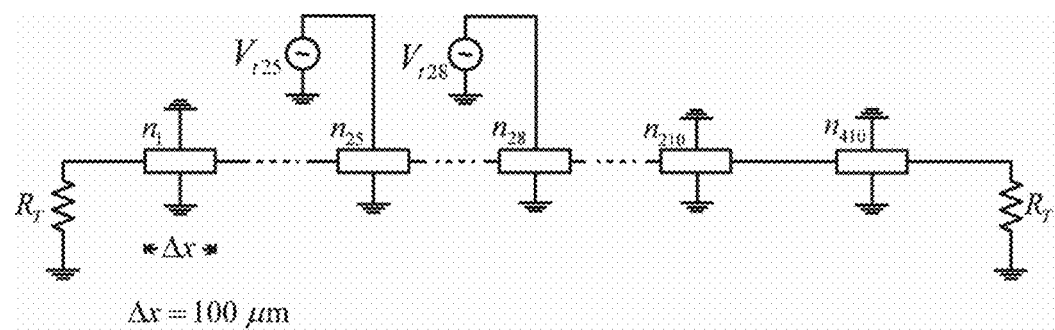
FIG. 8A shows the stimulation paradigm in a traveling-wave blocking stimulator. When energy is minimized, the timing and intensity of electrical stimulation amongst the electrodes is correlated with the timing of the action potential wave propagating in the nerve.
Figure 8B:
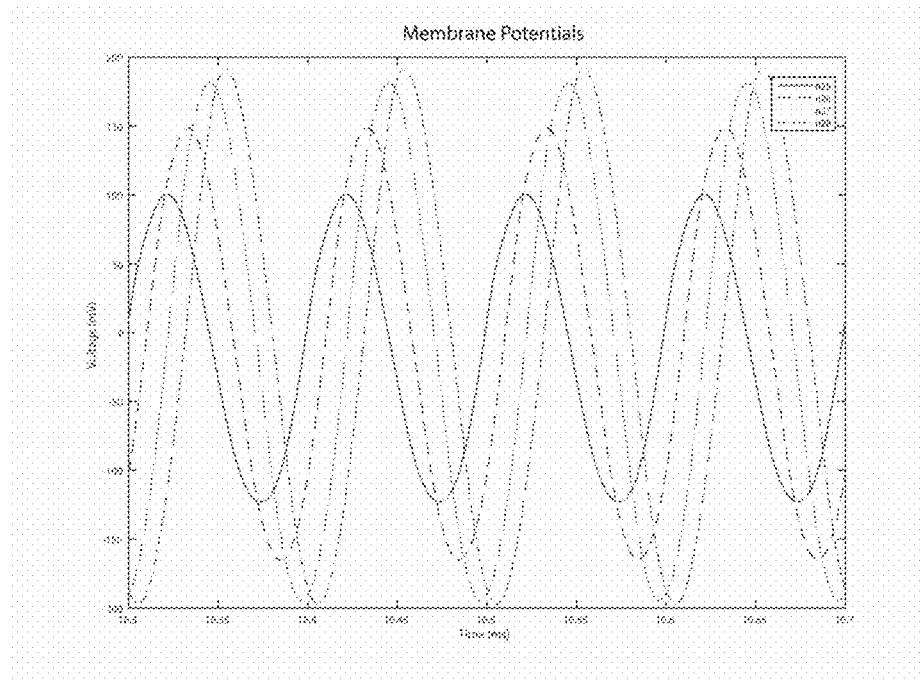
FIG. 8B shows how constructive interference amongst electrodes stimulated with appropriate phase delays can serve to sequentially build up signal strength within an axon.
Figure 8C:
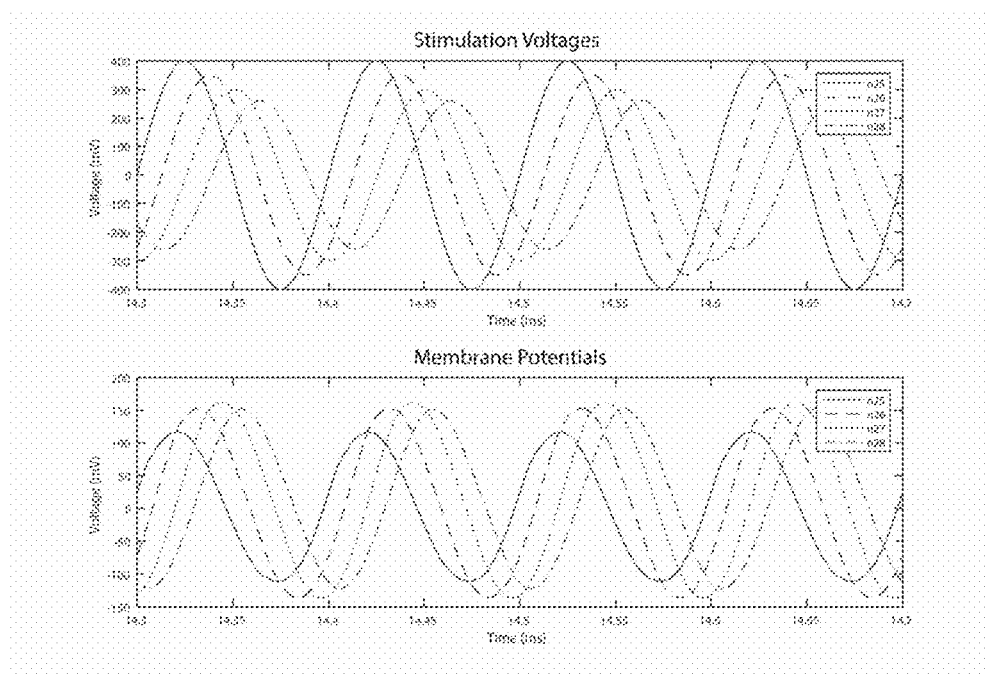
FIG. 8C shows that stimulation voltages can be sequentially lowered in a traveling-wave stimulator without causing the sequential membrane-potential buildup within the nerve to fall, thus saving energy.

FIG. 8A illustrates the key features of this embodiment in more detail. We applied stimulation voltages at the top membranes of the compartments $n_{25}$ to $n_{28}$ and recorded their bottom membrane potentials. FIG. 8B shows the result when we set $V_{t25}$-$V_{t28}$ to have the same amplitude while we chose their phases such that the stimulation voltage from each source is synchronized with the membrane potential wave that is propagating through the axon. Notice that the compartments further along the axon have their membrane potentials built up w.r.t their preceding compartments. FIG. 8C shows the result when we progressively decreased the amplitudes of $V_{t25}$-$V_{t28}$ but kept their phases synchronized with the propagating membrane potential wave; the top window shows the stimulation voltages on the $n_{25}$-$n_{28}$ compartments while the bottom window shows the potentials on their bottom membranes. Compared to the preceding compartments, the further compartments—with lower stimulation voltages on them—still exhibit similar levels of axonal excitation, thanks to the membrane potential wave that propagates from preceding compartments. Thus, with proper amplitude and timing control, the traveling-wave multi-electrode stimulation scheme allows us to excite a larger patch of axon, to increase the probability of blocking, with a low overall stimulation power.

Diagonal-Bridge Traveling-Wave Multi-Electrode Stimulation

Figure 9:
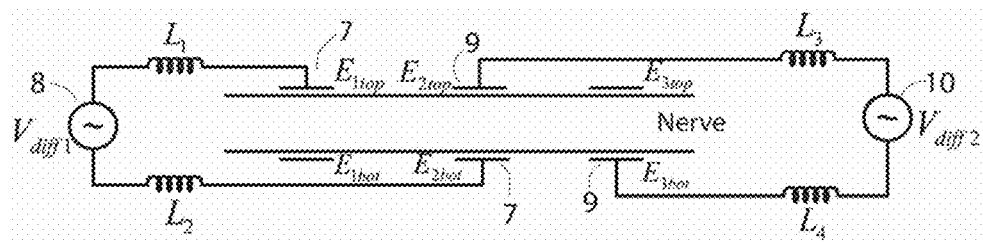
FIG. 9 shows a diagonal traveling-wave stimulation paradigm that helps spread current both laterally and across the nerve to increase the probability that unknown low-threshold sites are targeted by the stimulation but that the overall paradigm is still energy efficient.

To further increase the probability of blocking the action potential propagation in the nerve, we can extend the traveling-wave stimulation concept by exploiting the mechanical configurations of cuff electrodes on the nerve. The embodiment disclosed in FIG. 9, termed the diagonal-bridge traveling-wave multi-electrode stimulation, aims to maximize the effectiveness of the stimulation while avoiding high ohmic loss encountered in conventional schemes. Presented in FIG. 9 with only six electrodes without loss of generality, this diagonal-bridge stimulation scheme can be generalized to a higher number of electrodes to cover a larger patch of the nerve. Instead of applying anti-phasic stimulation waveforms across the vertically-separated electrodes as discussed in the original bridge-cuff stimulation of FIG. 4, we apply stimulation voltages 'diagonally': the $E_{1top}$-$E_{2bot}$ electrode pair 7 is stimulated differentially with the voltage source $V_{diff1}$ 8 while the $E_{2top}$-$E_{3bot}$ pair 9 is stimulated differentially with the voltage source $V_{diff2}$ 10. The stimulation current between each electrode pair is thus steered diagonally through the nerve, instead of laterally through the solution resistance, increasing the probability of modulating the ion channels of axons to elicit blocking. If the phase difference between $V_{diff1}$ 8 and $V_{diff2}$ 10 are controlled with sufficient resolution to keep the voltage differences between the top electrodes and between the bottom electrodes small, ohmic loss in the lateral solution resistance is minimized. In addition, if the phases of the stimulation voltage sources further along the nerve are synchronized with the membrane potential wave propagating along the axon, we can achieve the same traveling-wave amplification effect as discussed in the traveling-wave embodiment in the previous section.

Voltage Driver Design

A classic Class-E RF amplifier can be designed such that the transistor switches architect square-wave drives that are filtered by the resonant circuits. The switching is timed carefully to ensure that it always occurs when there is either zero voltage or zero current across the transistor thus minimizing loss. Such amplifiers can be nearly 100% efficient. An adaptive circuit described in M. Baker and R. Sarpeshkar, "Feedback Analysis and Design of RF Power Links for Low-Power Bionic Systems," Invited Paper, *IEEE Transactions of Biomedical Circuits and Systems*, Vol. 1, No. 1, pp. 28-38, April 2007 also ensures that the timing of the circuit adapts to changing load conditions preserving efficiency via pulsatile and clocked inputs. Thus, if we can record and decode from action potentials while stimulating, we can architect energy-efficient, adaptive, closed-loop stimulators including partial blocking. The use of clocks with phase delays allows digitally programmable control in actual experimental settings for bridge, traveling-wave, and other embodiments.

Multi-Electrode Resonant Stimulation Using Active Inductance

The use of passive inductors in our proposed resonant stimulation schemes enables energy recycling, shuttling energy back and forth between the capacitive and inductive forms. However, if the nerve presents a small capacitive loading to the electrode, the required passive inductance to achieve resonance at our targeted frequency (1 kHz-100 kHz) sometimes does not allow for a small-form-factor implementation.

Figure 10:
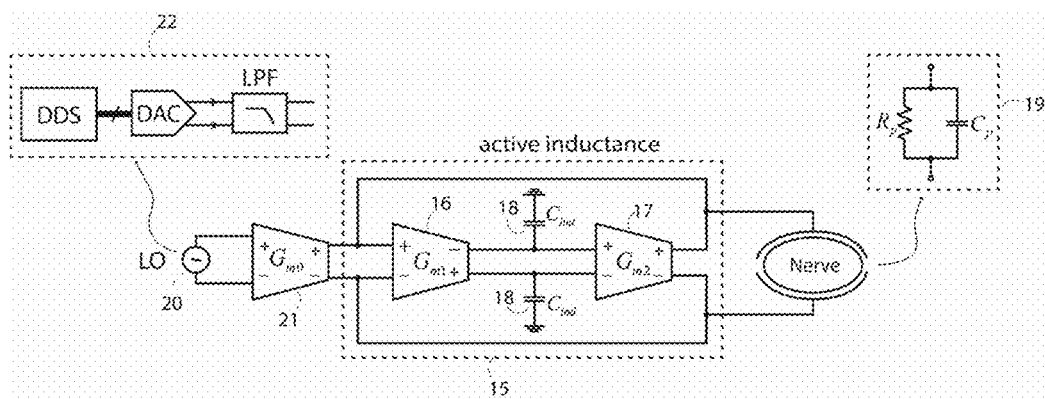
FIG. 10 shows how an active inductance implemented with a capacitance and active transconductors can replace passive inductances in all embodiments.

One popular technique to realize a large effective inductance is to electrically gyrate a capacitance using low-power operational transconductance amplifiers (OTA) to realize an active inductor. This technique is very attractive for low-power integrated circuit implementations as the entire stimulation circuitry can be integrated onto a single miniature chip. A fully-differential resonant stimulation circuit using an active inductor is shown in FIG. 10 to illustrate this embodiment. The active inductance 15 is realized by the $G_{m1}$ 16, $G_{m2}$ 17 OTAs and the two capacitors $C_{ind}$'s 18. This effective inductance appears in parallel with the nerve which can be modeled as a parallel $R_p$-$C_p$ network 19 using a standard series-to-parallel conversion of the effective nerve impedance. The local oscillator LO 20 generates a reference sinusoidal waveform from which the $G_{m0}$ OTA 21 converts into current to drive the RLC network. At the resonance frequency, the active inductance resonates with $C_p$ leaving only $R_p$ as the load of the $G_{m0}$ OTA. The voltage across the nerve thus depends on the amplitude of the $G_{m0}$ OTA's output current and the value of $R_p$, which can be made efficient via our cuff electrode design. Note that the LO 20 used in this scheme just provides amplitude and timing references for the stimulation voltage and does not drive the load directly. Due to the low frequency of the stimulation voltage relative to today's standards, the LO can be implemented in modern IC technologies with negligible power consumption compared to the stimulation power. For example, in FIG. 9, the LO is implemented with a direct digital synthesizer (DDS), a digital-to-analog converter (DAC), and a lowpass filter (LPF) 22 to provide very accurate amplitude and timing controls. As will be discussed below, the high-Q nature of the system and the inherent properties of the OTAs used for realizing the active inductor provide several benefits for the design of low-power multi-electrode blocking stimulation systems:

i) The active inductor helps resonantly amplify the stimulation voltage on the nerve, thus making it more likely to induce the nerve conduction block from a high-frequency current stimulator. With the active inductor absent, the nerve behaves as a parallel RC circuit and acts as a lowpass filter for stimulation currents, reducing stimulation effectiveness at high frequencies.

ii) It has been shown that a sinusoidal waveform is often more effective at inducing nerve conduction block. The active inductor makes the stimulator a narrowband circuit. If the ohmic loss in the electrode-nerve network is low through the careful electrode design, we can make the stimulator a very "high-Q" system. As a result, we can achieve a relatively pure sinusoidal stimulation waveform on the nerve from a "dirty" reference waveform of the LO 20 and let the high-Q stimulator filter out the unwanted harmonics. The DDS in the LO can be designed with a small memory while the DAC can be designed with low resolution and modest linearity, thus reducing the complexity and the overall power consumption of the LO.

iii) With a fixed bias current in each OTA, the stimulator is current limited, thus providing an automatic safety feature in the case of electrode shorting.

Figure 11:
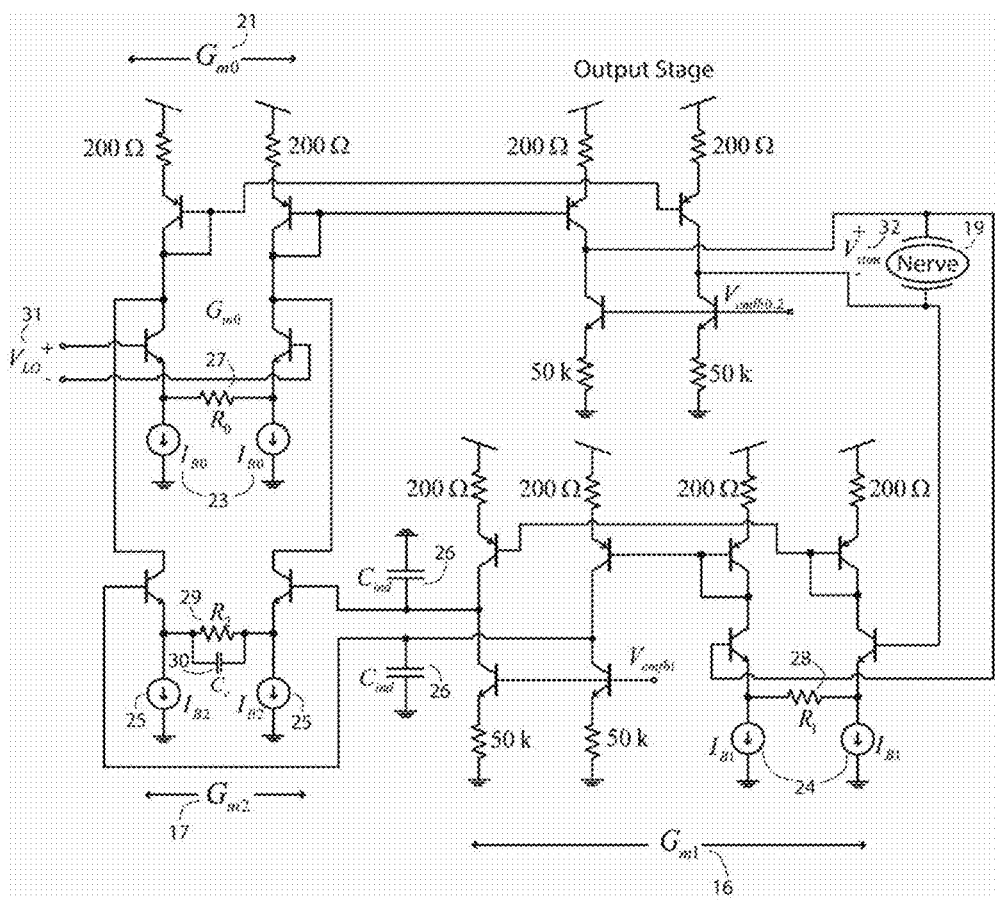
FIG. 11 shows a discrete circuit embodiment of an active inductance, which is used to perform resonant amplification on a nerve impedance with a capacitive reactance.

FIG. 11 shows an example discrete implementation of our active-inductor embodiment. The nerve 19 at the blocking frequency is represented by an equivalent impedance of 400-pF capacitance in parallel with a 50-kΩ resistance (a series impedance equivalent can also be used). All the OTAs are implemented with Bipolar Junction Transistors (BJT) from Analog Devices, Inc. (MAT14ARZ for NPN and SSM2220 for PNP). The bias currents $I_{B0}$ 23, $I_{B1}$ 24, and $I_{B2}$ 25 are 20 μA and the capacitance $C_{ind}$ 26 is 200 pF. The transconductance values of $G_{m0}$ 21, $G_{m1}$ 16, and $G_{m2}$ 17 OTAs are controlled by the degeneration resistances, $R_0$ 27, $R_1$ 28, and $R_2$ 29, respectively, all with a value of 15 kΩ in this design. The capacitance $C_c$ 30 is added in parallel with $R_2$ 29 to stabilize the overall feedback loop. Only the current of $G_{m2}$ OTA 17 needs to be sufficiently high to provide the stimulation current to the nerve. Since they are well known to those of ordinary skill in the art, Common-mode-feedback (CMFB) circuits are not shown in FIG. 11 to avoid clutter.

Figure 12A:
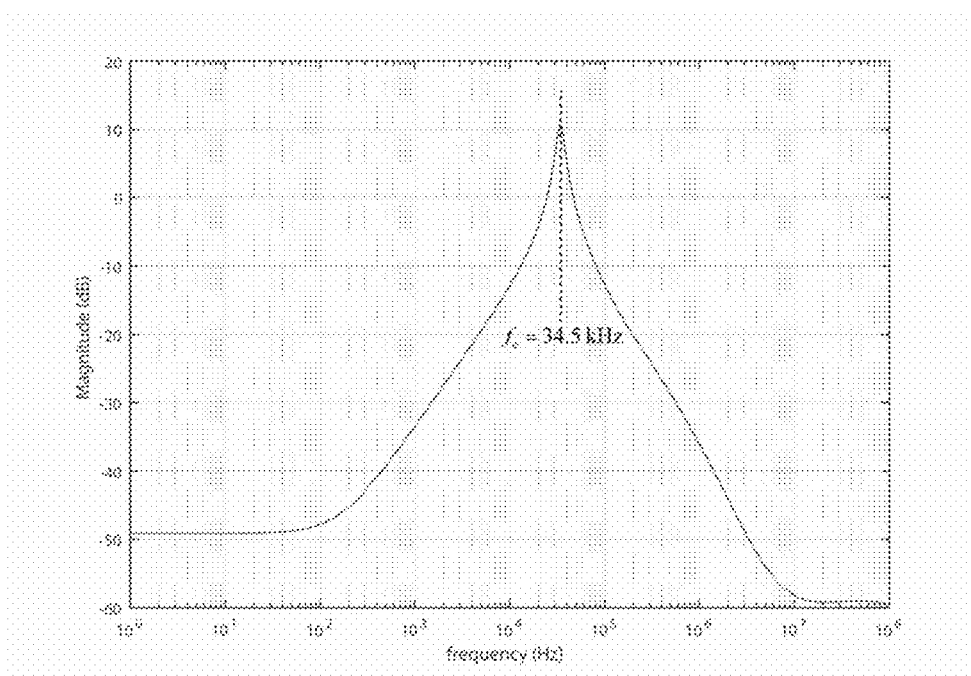
FIG. 12A shows resonant amplification in the embodiment of FIG. 11.
Figure 12B:
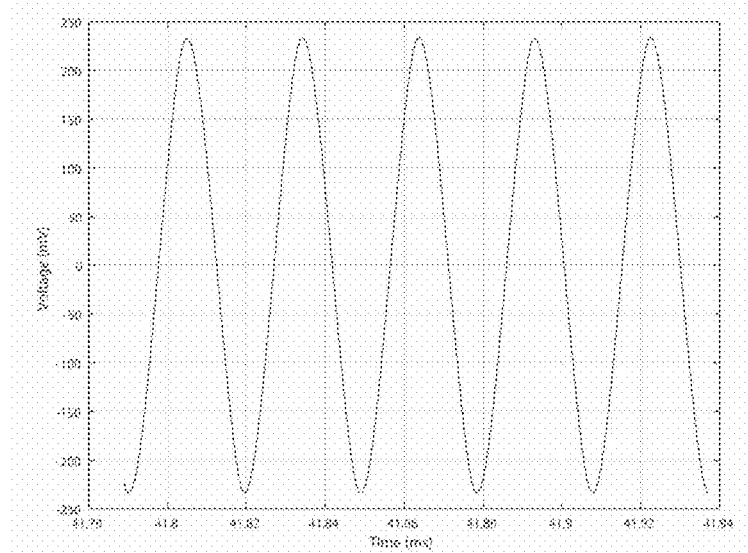
FIG. 12B shows the output stimulation voltage in the embodiment of FIG. 11.

FIG. 12A shows the magnitude response from $V_{LO}$ 31 to $V_{stim}$ 32. A sharp peak in the response at the resonance frequency of $f_c$=34.5 kHz is evident. FIG. 12B shows a differential voltage on $V_{stim}$ whose amplitude is 466 m$V_{pp}$. Due to the high-Q (high quality factor) nature of the resonant stimulator, $V_{stim}$ exhibits very little harmonic distortion. In cases where a larger $V_{stim}$ is needed, we can achieve a larger amplitude of $V_{stim}$ simply by increasing the input linear range of the $G_{m1}$ 16 OTA with well-known linearization techniques.

Active implementations of resonant blocking systems are not limited to the example embodiment that uses an active inductor, which is implemented with a gyrated capacitance and active transconductors as in FIG. 10. For example, other highly energy-efficient active transconductor-capacitor filter topologies that can achieve sharp resonances with large linear range in subthreshold circuit technology are explained in chapter 13 of R. Sarpeshkar, "Ultra Low Power Biolectronics: Fundamentals, Biomedical Applications, and Bio-inspired Systems", Cambridge University Press, 2010.

A Closed-Loop Architecture for Resonant Frequency Configuration

Figure 13:
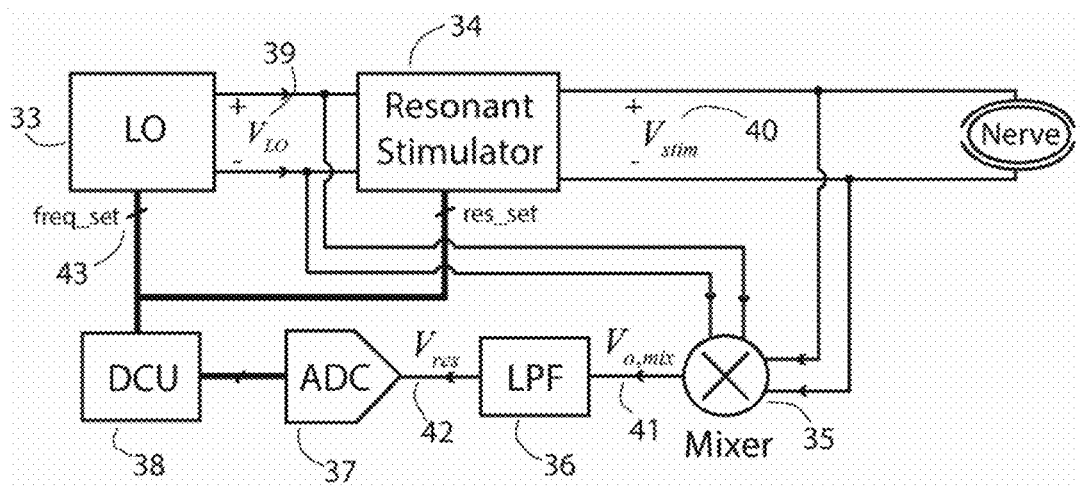
FIG. 13 shows how the resonant frequency of operation of a blocking stimulator can be adapted via a feedback and calibration loop.

The proposed resonant stimulator is a high-Q system which raises an important question: how do we stimulate right at the resonant frequency for the maximum blocking effectiveness? The nerve represents an unknown load to the stimulator, thus making it difficult to determine the resonant frequency of the system apriori. The embodiment of FIG. 13 reveals how we may detect the resonant frequency and configure the stimulator to operate at the optimum point for the blocking effectiveness and power consumption.

The architecture consists of an LO 33 and the resonant stimulator similar to the one in FIG. 10. We then add the calibration circuitry which consists of a mixer 35, a lowpass filter 36, a low-resolution/low-speed analog-to-digital converter (ADC) 37 and a digital control unit (DCU) 38. During calibration, the mixer 35 multiplies together the LO's reference waveform $V_{LO}$ 39 and the stimulation waveform $V_{stim}$ 40 to produce the signal $V_{o,mix}$ 41. At resonance, $V_{stim}$ 40 has the maximum amplitude and is in phase with $V_{LO}$ 39, thus producing the largest low-frequency component on $V_{o,mix}$ 41. The lowpass filter then extracts this low-frequency component ($V_{res}$ 42) and passes it, through the ADC 37, to the DCU 38. The DCU 38 then performs a search algorithm to find the optimum setting for the reference frequency of the LO and the resonant frequency of the stimulator—through setting the value of the freq_set bus 43 and the value of res_set bus 44—such that the closed-loop system produces the maximum value of $V_{res}$ 42. Assuming that the condition of the load changes slowly, we can heavily duty cycle the calibration (i.e., turning the calibration circuitry off when not in use): for instance, if the calibration is needed once every 10 seconds and each calibration takes approximately 10 ms, the duty-cycle ratio is only 1:1000, making the power required for the calibration circuit negligible compared to the actual stimulation power. In addition, for multi-electrode stimulation which consists of many nerve stimulators, the extra circuitry required for calibration (e.g. mixer, LPF, ADC, and DCU) can be time shared among all the stimulators, incurring only small area overhead per stimulator.

Highly-Configurable Closed-Loop Multi-Electrode Resonant Blocking System

Figure 14:
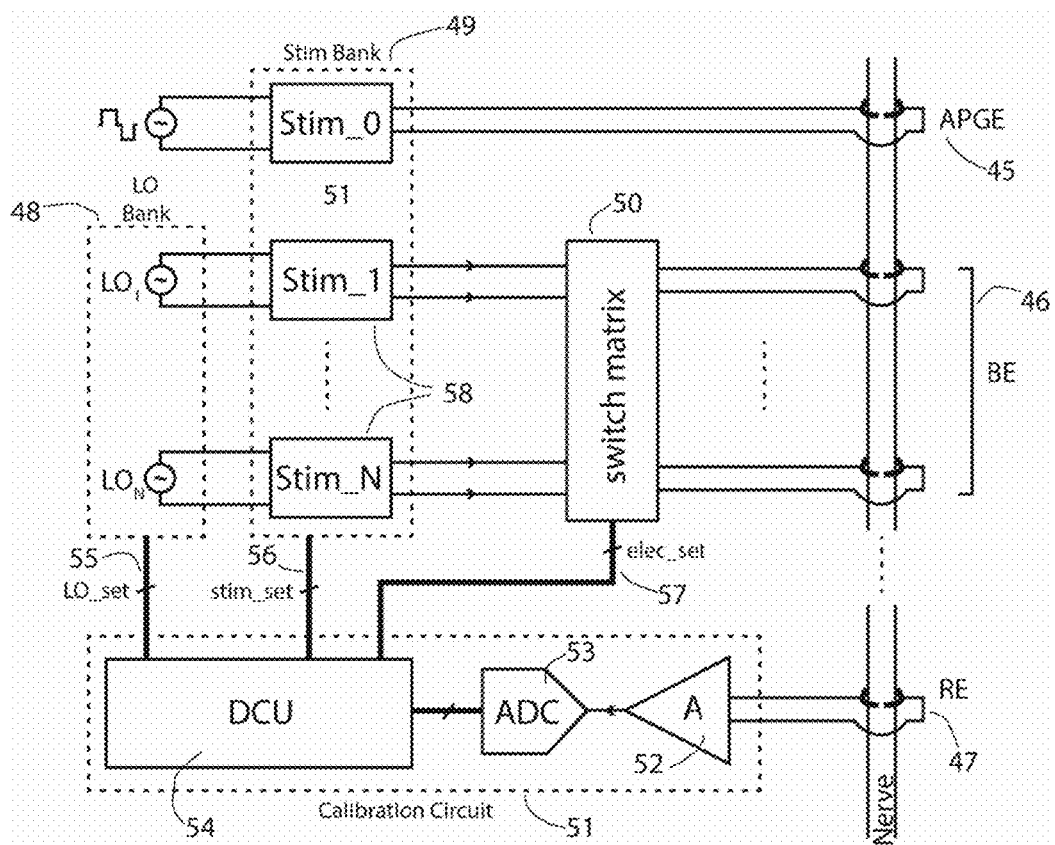
FIG. 14 shows the architecture of a highly-configurable, closed-loop, multi-electrode, resonant blocking system.

To efficiently block action potential propagation in practical medical devices, we need to optimize several parameters of the stimulation system such as the characteristics of the stimulation waveforms (e.g. amplitudes, phases, and frequencies) and the stimulation schemes (e.g., traveling-wave, diagonal-bridge traveling-wave). Therefore, an efficient blocking stimulator should be highly-configurable with the ability to calibrate itself for an optimum stimulation setting in terms of blocking effectiveness and power consumption. Towards this aim, FIG. 14 shows a highly-configurable closed-loop multi-electrode resonant blocking stimulation system. The system consists of three sets of electrodes—the Action Potential Generating Electrode (APGE) 45, the Blocking Electrodes (BE) 46, and the Recording Electrode (RE) 47—the LO bank 48, the stimulator bank 49, the switch matrix 50, and the calibration circuitry 51. The main function of the switch matrix 50 is to determine the connection between each stimulator and a pair of electrodes. With proper network design, the switch matrix allows the system to be configured as either a conventional bridge-cuff stimulator, a traveling-wave stimulator, or a diagonal-bridge traveling-wave stimulator—the choice of which is determined by the blocking effectiveness and power consumption.

During calibration, the stimulator Stim_0 51 stimulates the nerve through the APGE 45 and causes action potentials to propagate along the nerve. At the same time, the stimulators Stim_1-Stim_N 58 stimulate the nerve through the BE to block the action potential propagation. Located at a sufficient distance away from the BE 46 to minimize stimulation artifacts, the RE 47 records, via the nerve amplifier 52 and the ADC 53, action potentials that propagate from the APGE 45. The ADC 53 then digitizes the output of the nerve amplifier and identifies the presence of action potentials to the digital control unit (DCU) 54. The DCU 54 then applies a search algorithm to find the optimum setting of the stimulation system; it sets the characteristics of the waveforms via the LO_set bus 55, sets the drive strengths and resonant frequencies of the stimulators via the stim_set bus 56, and sets the electrode configurations via the elec_set bus 57 that controls the switch matrix 50, to identify the setting at which the action potential propagation is blocked with minimum power consumption.

Since conduction velocities of action potentials vary between nerve fibers of different diameters and amongst fascicles within larger nerves, the timing and intensity of traveling-wave stimulation can be adapted to block only certain desired fibers or at least lower the threshold for such blocking. Thus, our closed-loop multi-electrode systems can be not only energy efficient but also selective in targeting particular nerves, an important feature in many medical indications.

Embodiments of the Invention that Use Electromechanical Devices Such as Piezo-Electrets The innovations disclosed here can be generalized to other embodiments: For example, the inductor disclosed in our embodiments can be replaced with a piezo-electret, thus recycling nerve capacitive energy via mechanical energy and vice versa. Piezoelectrets are well-known devices to those in the art and form the basis for many energy-efficient quartz crystal oscillators. For example, they are described in Hillenbrand, J. and Sessler, G. M., "Piezoelectricity in cellular electret films," IEEE Transactions on Dielectrics and Electrical Insulation, Vol. 7, No. 4, pp. 537-542, August 2000.

Piezo-electrets may also be used to electrically actuate electrodes in synchrony with the stimulation such that either or both fluid flow and distance to the nerve are also oscillatory, further maximizing the chance that current flows into the nerve: Electrodes nearer to the nerve are more likely to send current into it; pushing fluid into the nerve while pulling it out elsewhere can dynamically modulate extracellular ohmic solution resistance in an advantageous configuration such that current is steered across the nerve rather than alongside it.

The mechanical, circuit, and stimulation strategies that we have disclosed serve to reduce power and energy dissipation for nerve-blocking stimulators in synergistic circuits and architectures.

What is claimed is:

1. An energy-efficient medical device composed of multiple distributed electrodes and circuits comprising distributed inductors said distributed electrodes electrically connected to said circuits with distributed inductors that generate electrical stimulation waveforms on the said electrodes, said electrodes adapted to be located transversely, above or below, and along an axial direction parallel to a nerve over a finite axial length, with said electrodes adapted to be located at a small distance from said nerve, said nerve propagating action potentials within it via natural traveling-wave action, said nerve having natural distributed nerve capacitance, wherein said electrical-stimulation waveforms on the multiple electrodes are configured with sequentially and monotonically varying axial timing delays or axial phase delays and with varying axial intensity with respect to each other by the circuits with distributed inductors such that signals of traveling action-potential waveforms along the axial length of said nerve nearby to the electrodes is correlated with said timing and intensity of said electrical-stimulation waveforms on the multiple electrodes such that energy efficiency of multi-electrode stimulation in the medical device is improved and wherein distributed electrical energy in said distributed nerve capacitance is effectively recycled in whole or in part by said circuits with distributed inductors creating said multi-electrode waveforms to further save multi-electrode electrical stimulation energy and wherein said distributed inductors also simultaneously amplify said distributed capacitive nerve energy via resonant action to a stimulation level that is sufficient to block action-potential propagation in the nerve.

2. The medical device of claim 1 wherein specific fibers with different action-potential traveling-wave propagation speeds in the nerve are preferentially blocked by adjusting the timing and intensity of the electrical stimulation waveforms generated by the circuits with distributed inductors.

3. The medical device of claim 1 further comprising additional distributed electrodes and a feedback or calibration loop wherein said electrodes configured to record action potentials from the nerve that serve as input signals to said feedback or calibration loop, and the recording of action potentials from the nerve causes the device to adapt the timing and intensity of its electrical stimulation waveforms via said feedback or calibration loop to maximize its energy efficiency.

4. The medical device of claim 1 wherein the multi-electrode stimulation is configured with varying axial phase and with varying transverse phase such that electrical current flow diagonally across the nerve increases, thus improving energy efficiency even when locations of low-threshold sites of nerve stimulation are uncertain.

5. The medical device of claim 1 that includes piezo-electret means of actuation for altering electrode distances from the nerve wherein such piezo-electret means of actuation are used to alter the distance of electrodes to the nerve in a manner correlated with the timing and intensity of the electrical stimulation waveforms generated by the circuits with distributed inductors to further improve energy efficiency of the overall multi-electrode stimulation.

6. The medical device of claim 1 wherein the inductors are passive electrical components.

7. The medical device of claim 1 wherein the inductors are implemented via active electrical components.

8. The medical device of claim 7 wherein the active electrical components are comprised of energy-efficient transconductor-capacitor circuits.

9. The medical device of claim 1 wherein piezo-electret devices in the electrode-stimulation circuits rather than inductors are adapted to perform both energy recycling and amplification.

10. An energy-efficient medical device composed of multiple distributed electrodes and circuits, with said electrodes connected to said circuits that generate electrical stimulation waveforms on the said electrodes with said electrodes adapted to be located transversely, above or below, and along an axial direction parallel to a nerve over a finite axial length and with said electrodes adapted to be located at a small distance from the nerve, said nerve propagating action potentials within it via natural traveling-wave action, said nerve having natural distributed nerve capacitance, wherein electrical-stimulation waveforms on the multiple electrodes are configured with sequentially and monotonically varying axial timing delays or axial phase delays and with varying axial intensity with respect to each other such that signals of traveling action-potential waveforms along the length of said nerve nearby to the electrodes is correlated with said timing and intensity of said electrical-stimulation waveforms on the multiple electrodes such that energy efficiency of multi-electrode stimulation in the medical device is improved and wherein the circuits that generate electrical-stimulation waveforms are configured to simultaneously minimize lateral extracellular voltage drops along the nerve while maximizing transverse current steered through the nerve such that energy efficiency of nerve blocking is improved.

11. The medical device of claim 10 wherein a multi-electrode topology with two transverse electrodes adapted to be located above and below the nerve, and with two identical transverse electrodes adapted to be located axially adjacent to said transverse electrodes create a device with four total electrodes in a bridge-like topology.

12. The medical device of claim 11 comprising a feedback or calibration loop wherein existent electrodes are adapted to record action potentials from the nerve, or further comprising additional electrodes that are adapted to record action potentials from the nerve, said recorded action potentials serving as input signals to said feedback or calibration loop, and wherein the recording of action potentials from the nerve causes the device to adapt the timing and intensity of its electrical stimulation waveforms via said feedback or calibration loop to maximize its energy efficiency.

13. The medical device of claim 10 wherein the multi-electrode stimulation is configured with varying axial phase and with varying transverse phase such that electrical current flow diagonally across the nerve increases, thus improving energy efficiency even when locations of low-threshold sites of nerve stimulation are uncertain.

14. The medical device of claim 10 that further includes insulating materials wherein said insulating materials are incorporated between transverse or axial electrodes to prevent current flow through extracellular paths across the nerve, thus further improving energy efficiency.

15. An energy-efficient medical device composed of multiple distributed electrodes that are electrically connected to a circuit that generates electrical stimulation to said electrodes, said electrodes adapted to be located transversely, above or below, and along an axial direction parallel to a nerve over a finite axial length and with all electrodes adapted to be located at a small distance from the nerve, said nerve propagating action potentials within it via natural traveling-wave action, said nerve having natural distributed nerve capacitance, wherein said circuit generating electrical-stimulation waveforms on the multiple electrodes creates said waveforms with sequentially and monotonically varying axial timing delays or axial phase delays and with varying axial intensity with respect to each other such that signals of traveling action-potential waveforms along the length of said nerve nearby to the electrodes is correlated with said timing and intensity of said electrical-stimulation waveforms on the multiple electrodes such that energy efficiency of multi-electrode stimulation in the medical device is improved and wherein electrical stimulation is delivered to simultaneously minimize lateral extracellular voltage drops along the nerve.

16. The medical device of claim 15 wherein a bridge-like multi-electrode topology is formed by four electrodes, with two transverse electrodes adapted to be located above and below the nerve, and with two identical transverse electrodes adapted to be located axially adjacent to said transverse electrodes.

17. The medical device of claim 15 comprising a feedback or calibration loop wherein existent electrodes are adapted to record action potentials from the nerve, or further comprising additional electrodes that are adapted to record action potentials from the nerve, said recorded action potentials serving as input signals to said feedback or calibration loop and wherein the recording of action potentials from the nerve causes the device to adapt the timing and intensity of its electrical stimulation waveforms via said feedback or calibration loop to maximize its energy efficiency.

* * * * *